United States Patent [19]

Pastorek et al.

[11] 4,228,083
[45] Oct. 14, 1980

[54] PROCESS FOR THE PRODUCTION OF β-(5-NITRO-2-FURYL)-ACROLEIN

[75] Inventors: Emmerich Pastorek, Hemsbach; Winfried Orth, Hassloch; Werner Fickert, Mannheim, all of Fed. Rep. of Germany

[73] Assignee: Rutgerswerke Aktiengesellschaft, Frankfurt am Main, Fed. Rep. of Germany

[21] Appl. No.: 92,324

[22] Filed: Nov. 8, 1979

[30] Foreign Application Priority Data

Dec. 21, 1978 [DE] Fed. Rep. of Germany ....... 2855245

[51] Int. Cl.$^3$ .......................................... C07D 307/71
[52] U.S. Cl. ................................................. 260/347.8
[58] Field of Search ...................................... 260/347.8

[56] References Cited

U.S. PATENT DOCUMENTS 3,491,123  1/1970  Ventor et al. .................... 260/347.8

*Primary Examiner*—Richard Raymond
*Attorney, Agent, or Firm*—Hammond & Littell, Weissenberger and Muserlain

[57] ABSTRACT

An improved process for the production of β-(5-nitro-2-furyl)-acrolein by reacting 5-nitro-furfural and acetaldehyde in the presence of a secondary amine, the improvement comprises effecting the reaction in an aliphatic carboxylic acid of 2 to 4 carbon atoms.

9 Claims, No Drawings

PROCESS FOR THE PRODUCTION OF β-(5-NITRO-2-FURYL)-ACROLEIN

STATE OF THE ART

β-(5-nitro-2-furyl)-acrolein is a well known starting material for the production of pesticidal compounds having fungicidal and bactericidal activity and which are useful in the pharmaceutical and textile industries and in agriculture. Usually, β-(5-nitro-2-furyl)-acrolein is prepared by reacting 5-nitro-furfural and acetaldehyde in the presence of a secondary amine with or without an inert organic solvent. German AS No. 1,493,890 and U.S. Pat. No. 3,491,123 describe the reaction using benzene as the solvent with low yields of 30 to 36%. The use of benzene as the solvent has the disadvantages of being toxic and of insufficiently dissolving the resins formed in the reaction in relatively large quantities which leads to processing difficulties such as clogging of the reaction apparatus with the semi-solid resins.

Other methods for the preparation of β-(5-nitro-2-furyl)-acrolein are known such as those described in U.S. Pat. No. 2,799,686, Japanese Patent application No. 15,635 (62), Chem, Abs., Vol. 59, p. 9986c and French BSM No. 1970M. However, all the said processes have various disadvantages such as poor yields, starting materials and non-feasibility of industrial production.

OBJECTS OF THE INVENTION

It is an object of the invention to provide a simple, industrial process for the production of β-(5-nitro-2-furyl)-acrolein in good yields.

This and other objects and advantages of the invention will become obvious from the following detailed description.

THE INVENTION

The novel process of the invention for the preparation of β-(5-nitro-2-furyl)-acrolein comprises reacting 5-nitro-furfural and acetaldehyde in the presence of a secondary amine with an aliphatic carboxylic acid of 2 to 4 carbon atoms as the solvent. Preferably, the reaction is effected at $-10°$ to $90°$ C., most preferably at $10°$ to $80°$ C. The molar ratio of 5-nitro-furfural to acetaldehyde is 1:1 to 1:2, preferably 1:1.6 to 1:1.8. The amount of amine is usually 0.02 to 0.2 moles per mole of 5-nitro-furfural.

Examples of suitable secondary amine catalysts are secondary amines of the formulae

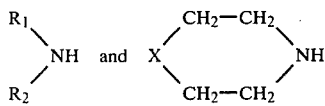

wherein $R_1$ and $R_2$ are individually selected from the group consisting of lower alkyl, hydroxy lower alkyl, lower alkoxyalkyl, lower alkenyl, cycloalkyl of 5 to 7 carbon atoms, aryl and aryl lower alkyl and X is selected from the group consisting of —O—, —S—, —NH—, —CH₂—and

and Alk is lower alkyl. Lower is intended to indicated 1 to 7 carbon atoms. X may also be in the 2- or 3-position of the ring rather than the indicated 4-position and the cyclic ring may be a 5 or 7 member ring substituted on a cyclic ring carbon atom.

Examples of specific groups for $R_1$ and $R_2$ are lower alkyl such as methyl, ethyl, propyl, isopropyl, butyl, isobutyl and hexyl, hydroxy lower alkyl such as hydroxyethyl and 1-methyl-2-hydroxy-ethyl, lower alkoxyalkyl such as methoxy-ethyl, ethoxyethyl and butyloxyethyl, lower alkenyl such as allyl, cycloalkyl such as cyclopentyl, cyclohexyl and methylcyclohexyl, aryl such as phenyl and lower alkylphenyl and aralkyl such as benzyl and phenethyl.

Examples of suitable aliphatic carboxyli acids of 2 to 4 carbon atoms useful as the solvent for the reaction are acetic acid, propionic acid, butyric acid and isobutyric acid. The acid may be in the anhydrous form but is preferably used as a 20 to 80% aqueous acid solution.

In the following examples there are described several preferred embodiments to illustrate the invention. However, it should be understood that the invention is not intended to be limited to the specific embodiments.

EXAMPLE 1

148.4 g (1 mole) of 95% 5-nitro-furfural were dissolved under a nitrogen atmosphere in 400 ml of 60% acetic acid and after cooling the solution to 0° C., 72.8 g (1.8 moles) of acetaldehyde were added thereto with stirring. Then, a solution of 0.088 moles of 33% aqueous dimethylamine solution and 20 ml of 60% acetic acid was added dropwise over 10 minutes with vigorous stirring to the reaction mixture at 5° to 10° C. The mixture was heated to 60° C. over 90 minutes and was then stirred at 60°–65° C. for 2½ hours. The mixture was cooled to 18° C. and was then vacuum filtered and the recovered product was washed with a small amount of 60% acetic acid or isopropanol and was dried to obtain 88.6 g (53% yield) of β-(5-nitro-2-furyl)-acrolein in the form of yellow to ocher fine crystals melting at 111.5° to 113.5° C.

EXAMPLES 2 TO 12

The procedure of Example 1 was repeated for Examples 2 to 12 except that the catalyst and the amount thereof were changed as indicated in Table I. The yields and melting points of the β-(5-nitro-2-furyl)-acrolein product are reported in Table I.

TABLE 1

| Example | g/mole catalyst | Catalyst | Yield in g | in % | M.p. °C. |
|---|---|---|---|---|---|
| 2 | 12 /0.093 | Dibutylamine | 110 | 65.8 | 113–115 |
| 3 | 12 /0.065 | Dicyciohexylamine | 78 | 46.7 | 114–116 |
| 4 | 7 /0.035 | Dibenzylamine | 83 | 49.6 | 105–110 |
| 5 | 6 /0.057 | Diethanolamine | 130 | 77.8 | 113–115.5 |
| 6 | 12 /0.090 | Di(2-hydroxy-propyl)-amine | 126 | 75.4 | 112–115.5 |
| 7 | 5 /0.066 | Methyl-ethanol-amine | 126 | 75.4 | 111–114.5 |
| 8 | 9 /0.067 | Di(methoxyethanol)-amine | 87 | 52.1 | 107.5–113 |
| 9 | 4 /0.046 | Morpholine | 99 | 59.2 | 110–113 |
| 10 | 6 /0.058 | Thiomorpholine | 105 | 62.8 | 107–111 |
| 11 | 10 /0.112 | Piperidine | 80 | 47.9 | 111–114 |

TABLE 1-continued

| Example | g/mole catalyst | Catalyst | Yield in g | in % | M.p. °C. |
|---|---|---|---|---|---|
| 12 | 2.5/0.028 | 1-Methylpiperazine | 91 | 54.5 | 113–115 |

EXAMPLES 13 TO 17

The procedure of Example 1 was followed with 6 g (0.057 mole) of diethanolamine as catalyst and 75 g (1.7 moles) of acetaldehyde per mole of 5-nitro-furfural with the amounts of alkanoic acid recited in Table II which also reports the yields and melting point of β-(5-nitro-2-furyl)-acrolein.

TABLE II

| Example | Solvent | ml | % | Reaction time (min.) | temp. °C. | Yield g | % | M.P.°C. |
|---|---|---|---|---|---|---|---|---|
| 13 | Acetic acid | 580 | 30 | 90 | 65 | 78 | 46.7 | 114–116 |
| 14 | Acetic acid | 350 | 99 | 90 | 65 | 130 | 77.8 | 102–110 |
| 15 | Acetic acid | 400 | 60 | 45 | 75–80 | 112 | 67.0 | 114–116 |
| 16 | Propionic a. | 400 | 60 | 120 | 65 | 129 | 77.2 | 108–110 |
| 17 | Isobutyric acid | 450 | 70 | 150 | 65 | 127 | 76.0 | 103–108 |

Various modifications of the process of the invention may be made without departing from the spirit or scope thereof and it is to be understood that the invention is to be limited only as defined in the appended claims.

We claim:

1. An improved process for the production of β-(5-nitro-2-furyl)-acrolein by reacting 5-nitro-furfural and acetaldehyde in the presence of a secondary amine, the improvement comprises effecting the reaction in an aliphatic carboxylic acid of 2 to 4 carbon atoms.

2. The process of claim 1 wherein the molar ratio of 5-nitro-furfural to acetaldehyde is 1:1 to 1:2.

3. The process of claim 2 wherein the ratio is 1:1.6 to 1:1.8.

4. The process of claim 1 wherein the reaction is effected at −10° to 90° C.

5. The process of claim 1 wherein the reaction is effected at 10° to 80° C.

6. The process of claim 1 wherein the acid is anhydrous.

7. The process of claim 1 wherein the acid is 20 to 80% aqueous acid solution.

8. The process of claim 1 wherein the acid is aqueous acetic acid.

9. The process of claim 7 wherein the acid is selected from the group consisting of acetic acid, propionic acid, butyric acid and isobutyric acid.

* * * * *

UNITED STATES PATENT AND TRADEMARK OFFICE
CERTIFICATE OF CORRECTION

PATENT NO. : 4,228,083

DATED : October 14, 1980

INVENTOR(S) : Emmerich Pastorek et al

It is certified that error appears in the above—identified patent and that said Letters Patent is hereby corrected as shown below:

Column 2, line 59, Table 1: "Dicyciohexylamine"

should read -- Dihexylamine --.

Signed and Sealed this

Twenty-eighth Day of April 1981

[SEAL]

Attest:

RENE D. TEGTMEYER

Attesting Officer     Acting Commissioner of Patents and Trademarks